United States Patent [19]

Bryan et al.

[11] Patent Number: 4,742,154
[45] Date of Patent: May 3, 1988

[54] GLN- OR ASN-VASOPRESSIN COMPOUNDS

[75] Inventors: William M. Bryan, Philadelphia; William F. Huffman, Malvern; Michael L. Moore, Media, all of Pa.

[73] Assignee: Smithkline Beckman Corporation, Philadelphia, Pa.

[21] Appl. No.: 790,666

[22] Filed: Oct. 23, 1985

[51] Int. Cl.$^4$ .................. A61K 37/00; C07C 103/52
[52] U.S. Cl. .................. 530/315; 530/328; 530/329; 514/807
[58] Field of Search .............. 530/315, 329, 328; 514/16, 17, 807

[56] References Cited

U.S. PATENT DOCUMENTS 4,469,679  9/1984  Huffman et al. .............. 514/11
4,481,193 11/1984  Ali et al. .............. 514/11
4,481,194 11/1984  Ali et al. .............. 514/11

OTHER PUBLICATIONS

M. Manning et al., Nature, 308 652 (1984).

Primary Examiner—Delbert R. Phillips
Assistant Examiner—Nathan M. Nutter
Attorney, Agent, or Firm—Linda E. Hall; Janice E. Williams; Alan D. Lourie

[57] ABSTRACT

Peptides whose structures resemble those of vasopressin antagonists but have both a carboxamido amino acid unit and a basic amino acid unit in the side chain have good antagonist activity. A species of the invention is [1-($\beta$-mercapto-$\beta$,$\beta$-cyclopentamethylenepropionic acid)-2-(O-ethyl)-D-tyrosine-4-valine-8-glutamine-9-desglycine]-vasopressin.

12 Claims, No Drawings

GLN- OR ASN-VASOPRESSIN COMPOUNDS

This invention relates to certain peptides which are related in structure to the hormone, vasopressin, but which antagonize the latter's activity. The compounds of this invention are characterized by having structures which have both a glutamine-like unit and an arginine-like unit in the side chain of the vasopressin antagonist structure.

BACKGROUND OF THE INVENTION

M. Manning et al., Nature, 308 652 (1984) and U.S. Pat. No. 4,469,679 have disclosed that the terminal glycine unit at the 9-position of certain vasopressin-like antagonists can be removed or replaced by L or D-Ala, Ser or Arg without necessarily affecting binding at vasopressin receptors.

U.S. Pat. Nos. 4,481,194 and 4,481,193 disclose that removing proline at position 7 or both proline and glycine at positions 7 and 9 from the structures of vasopressin antagonists gives compounds which retain substantial, but somewhat reduced, antagonist activity.

The vasopressin-like compounds of this invention have structures which are distinguished over those of the prior art in that the side chain contains both a basic amino acid and a carboxamido-containing amino acid as side chain units attached, directly or through a proline unit to a disulfide VSP-like ring. The carboxamido group is at a position other than the preferred amido at the C-terminus. Thusly, the compounds of this invention have a receptor site-seeking side chain which contains two potential sites for binding. These are a basic site such as that in Arg or Lys as well as an internal carboxamido site such as that in Gln or Asn. The resulting compounds are potent vasopressin antagonists.

In the description herein and in the claims, the nomenclature common in the art of peptide and vasopressin chemistry is used. When no configuration is noted, the amino acid unit is in the L, or naturally occurring, form. In certain structural formulas, the thio members of the Pmp, Tmp and Cys units are added for clarity.

Certain of the peptide art designations used herein are the following: Pmp, β-mercapto-β,β-cyclopentamethylenepropionic acid; Tmp, β-mercapto-β,β-cyclotetramethylenepropionic acid; Tyr(Alk), O-alkyltyrosine; Phe(Alk), 4-alkylphenylalanine; Gln, glutamic acid amide or glutamine; Tyr, tyrosine; Phe, phenylalanine; Val, valine, Ile, isoleucine; Lys, lysine; Arg, arginine; Asn, asparagine; Tos, tosylate; BHA, benzhydrylamine; DMAP, 4-dimethylaminopyridine; DIEA, diisopropylethylamine; HF, hydrogen fluoride; 4-MeBzl, 4-methylbenzyl; TFA, trifluoroacetic acid; DCC, dicyclohexylcarbodiimide; Boc, t-butyloxycarbonyl; Z, benzyloxycarbonyl; VSP, vasopressin; HOBT, hydroxybenzotriazole; ACM, acetamidomethyl. The critical glutamine or asparagine units are also written as Glu(NH$_2$) or Asp(NH$_2$).

"Alk" represents a lower alkyl of 1-4 carbons. For example, these may be optionally attached to the 4-oxygen substituent of a tyrosine unit or to the p-position of a phenylalanine which may be present at unit position 2. Such alkyl substituents include methyl, ethyl, n-propyl, isopropyl or butyl. Ethyl is preferred. When the term, "vasopressin", is used, it means L-arginine vasopressin (AVP) unless otherwise modified.

DESCRIPTION OF THE INVENTION

The peptide compounds of this invention are illustrated by the following structural formula:

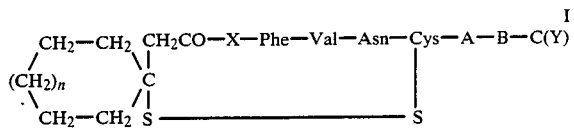

in which:
A is Pro or a single bond;
X is a D or L isomer of Ile, Tyr, Tyr(Alk) or Phe(Alk);
Y is NH$_2$ or OH;
n is 0 or 1;
B is a D or L isomer of Gln, Asn, Lys or Arg; and
C is a D or L isomer of Gln, Asn, Lys or Arg, one of B and C being either Gln or Asn and one being either Lys or Arg, or a pharmaceutically acceptable salt or ester prodrug thereof.

A subgeneric group of compounds of this invention comprises compounds of formula I in which B is Gln and Y is NH$_2$.

The compounds of this invention, therefore, are characterized by structures which have a Gln[NH$_2$COCH$_2$CH$_2$(NH$_2$)CO$_2$H] or an Asn[NH$_2$COCH$_2$CH(NH$_2$)CO$_2$H] as a unit in the di- or tripeptide tail in the vasopressin-like structure. The C-terminal units are preferably in the amide form (Y is NH$_2$).

Also included in this invention are compounds of formula I whose structures have a higher homologous unit in place of the side chain Asn or Gln units. In these, the carboxamido is separated from the α-position by a propylene or butylene chain.

Also included in this invention are addition salts, complexes, such as solvates or ester prodrugs of the compounds of this invention. The nontoxic, pharmaceutically acceptable acid addition salts are preferred. Such acid addition salts are prepared in standard manner for example reacting the parent base compound in a suitable solvent with an excess of an acid, such as hydrochloric, hydrobromic, sulfuric, phosphoric, acetic, maleic, succinic, ethanedisulfonic or methanesulfonic acids. The compounds of this invention are often isolated as the acetate salts. The ester derivatives of the acid forms of the end products, such as the methyl, ethyl or benzyl esters, are prepared as known to the art. Alkali metal salts are also prepared as known to the art when the C-terminus is in acid form.

The end products (I) of this invention are prepared by oxidation of the following linear heptapeptides:

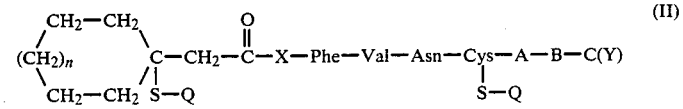

in which X, A, n, B and C and Y are as defined for formula I above or protected forms thereof. The mercapto groups are members of the units at positions 1 and 6. Each Q is hydrogen or a displaceable protective group such as acetamidomethyl (ACM). The dithiol of formula II may be also oxidized in the form of an ester or amide derivative of the unit at the C-terminal position. For example, the amide may be those peptides of Formula II in which Y is $NH_2$. The esters would have Y as OAlk or OBzl.

Said oxidation is carried out using an excess of an alkali metal ferricyanide, such as potassium or sodium ferricyanide, with the linear intermediate II. A suitable unreactive solvent, preferably an aqueous-miscible solvent at a neutral pH, about 7–7.5, is used. Reaction is carried out at ambient temperature or lower until the reaction is substantially complete. Preferably, the concentrations of the linear peptide dimercaptan and the oxidizing agent are low, say 0.01–0.1 molar concentration of oxidizing agent in several liters of aqueous solution to cyclize 1–5 grams of dimercaptan.

Other mild oxidation agents having an oxidation potential roughly equivalent to ferricyanide may also be used for the ring closure reaction. Oxygen passage through the reaction solution for several days, diiodoethane, iodine in methanol, hydrogen peroxide or oxidation in the presence of cupric salts are such alternatives. Cyclization, also, occurs when a displaceable, thiol-protective group such as that at the mercaptan group of the Pmp unit is displaced intramolecularly.

An especially useful thio protective group is acetamidomethyl (ACM). Iodine/alcohol is used for direct, one-pot cyclization of the bis-ACM-S linear peptide.

Of course, one skilled in the art will recognize that certain cyclization methods are not appropriate if an interfering reaction site is present in the structure of the starting material of formula II. The linear peptide starting material may have protective groups common to the art temporarily present at the various linear units.

The peptide chain of the linear peptides is usually built up, stepwise, proceeding from the C unit and working toward the Pmp unit. Each unit is properly protected as known in the peptide art and as described herein. The sequence of step-reactions is conveniently carried out in a Beckman 990B peptide synthesizer or its equivalent without isolation of each intermediate peptide. The details of the procedure are in the working examples presented hereinafter.

The various amino acids (AA), which are consecutively added to the resin-supported chain, are protected as known to the art. For example, the Boc protecting group is used for an amino group, especially at the α-position; an optionally substituted benzyl, for the mercapto groups at the Pmp or Tmp units; a tosyl for the Arg unit; and an optionally substituted carbobenzyloxy (Z) for the Tyr or Lys units. The protective groups are, most conveniently, those which are not easily removed by using mild acid treatment, such as for removing the Boc group. Rather one should use HF, sodium-liquid ammonia or, for benzyl or carbobenzyloxy groups, catalytic hydrogenation.

Preferably, the glutamine or asparagine units are used in the form of the Boc derivative at the α-amino group with no protective groups at the critical carboxamido group. Various amido protective groups may, however, be used to minimize side-reaction or to increase solubility of the peptide reactants. Exemplary of these and their removal conditions are the following: xanthhydryl (acid stable); 2,4-dimethoxybenzyl (TFA or HF); 4-methoxybenzyl (HF); 4,4'-dimethoxybenzhydryl (TFA).

The resin supported peptide is then treated with an excess of anhydrous hydrogen fluoride with an appropriate scavenger compound, such as anisole, to give the linear peptide intermediate of formula II in good yield.

The end compounds of the invention have excellent $V_2$ vasopressin antagonist activity. Vasopressin is known to contribute to the anti-diuretic mechanism of action within the kidney. When the action of these compounds antagonizes that of the natural anti-diuretic hormone (ADH), the body excretes water due to an increased permeability of the terminal portions of the renal tubule. The mechanism of action is at the vasopressin receptors. ($V_2$-receptors) located on the plasma membrane of certain renal epithelial cells. The most notable pharmacodynamic effect of the ADH antagonists of the invention is that of a water diuretic rather than of a natriuretic such as hydrochlorothiazide.

Any patient suffering from the syndrome of inappropriate antidiuretic hormone secretion (SIADH) or from an undesirable edematous condition is a target for the claimed compounds. Examples of clinical conditions indicated for the compounds of this invention include hypertension, hepatic cirrhosis, hyponatremia, congestive heart failure or a component of any traumatic condition resulting from serious injury or disease.

The second group of vasopressin receptor sites are the vascular pressor sites ($V_1$-receptors) within the cardiovascular system itself. These may also be antagonized by the compounds of this invention, often to a lower degree.

The compounds of this invention, therefore, are used especially to induce vasopressin antagonism resulting in anti-hypertensive or diuretic activity in patients in need of such treatment. The latter treatment comprises the administration internally, for example parenterally, bucally or by insufflation, of a nontoxic but effective quantity of the chosen compound, preferably dispersed in a pharmaceutical carrier. Dosage units of the active ingredient are selected from the range of 0.01 to 10 mg/kg, preferably 0.1 to 1 mg/kg, of base based on a 70 kg patient. The dosage units are administered to the human or animal patient in need of treatment from 1 to 5 times daily.

The pharmaceutical compositions of this invention, which contains an active antagonist ingredient of formula I, comprises a dosage unit of the active ingredient which is dissolved or suspended in a standard liquid carrier, such as isotonic saline, and is contained in an ampoule or a multiple dose vial suitable for a parenteral injection such as for intravenous, subcutaneous or intramuscular administration. A composition for insufflation may be similar but is usually administered in a metered dose applicator or inhaler. Pulverized powder compositions may, also, be used along with oily preparation, gels, buffers for isotonic preparations, buccal losenges, trans-dermal patches and emulsions or aerosols.

$V_2$-antagonistic activity toward the natural anti-diuretic hormone (anti-ADH activity) is determined, in vitro, in the medullary tissue of hog or human kidneys and, in vivo, in the hydropenic rat. The protocols for the in vitro assay of compounds using vasopressin stimulated adenylate cyclase activation or vasopressin binding activity are described by F. Stassen et al., J. Pharmacology and Experimental Therapeutics, 223, 50–54 (1982). This reference, on page 53, column 2 also describes the unpredictability of activity in this field.

The assay for anti-ADH activity in vivo is the hydropenic rat protocol described below:

Hydropenic Rat Screen

Food and water are removed from male rats approximately 18 hours prior to testing. Animals are housed 4 per metabolism cage. At 0 hour, the test compound is administered intraperitoneally to the test group and an equivalent volume of vehicle is administered to both control groups (fasted and non-fasted). Urine volume and osmolality are measured every hour for 4 hours. Test values are recorded as ml of urine excreted (cumulative), mEg/rat electrolyte excreted, mg/rat urea excreted, and osmolality in milli-Osmoles/Kg $H_2O$. A tolerance test is used to determine significance. $ED_{300}$ is defined as the dose of compound ($\mu g/kg$) required to lower urine osmolality to 300 m-Osmoles/kg.

TABLE 1

Pmp—D—Tyr(Et)—Phe—Val—Asn—Cys—X

| | Kb (nM) | Ki (nM) | $ED_{300}$ ($\mu g/kg$) |
|---|---|---|---|
| (A) ProGlnArg($NH_2$) | 7.4 | 9.4 | 41.3 |
| (B) ProArgGly($NH_2$) | 7.4 | 6.7 | 11.2 |
| (C) ProArg($NH_2$) | 12 | 4.5 | 9.2 |

The following examples are intended to demonstrate the preparation and use of the compounds of this invention. All temperatures are in degrees Centigrade.

EXAMPLE 1

Pmp—D—Tyr(Et)—Phe—Val—Asn—Cys—Pro—Gln—Arg($NH_2$)

The protected peptide intermediate resin, Pmp(4-MeBzl)-D-Tyr(Et)-Phe-Val-Asn-Cys(4-MeBzl)-Pro-Gln-Arg(Tos)-BHA was synthesized by solid-phase methods on benzhydrylamine resin (BHA). On a shaker, 1.0 mmol of the BHA-resin was used. All amino acids were protected as tert.-butyloxycarbonyl (Boc) on the α-nitrogen and, then, coupled sequentially as follows:
1. (2×) BocArg(Tos); MW 428; 3 mmole=1.28 g; 6 mmole HOBT=0.81 g.
2. (2×) BocGln; MW 246; 3 mmole=0.74 g; 9 mmole HOBT=1.21 g.
   The Boc group was removed manually by addition of 2×35 ml of 4N HCl/Dioxane.
3. (2×) BocPro; MW 215; 3 mmole=0.64 g; 6 mmole HOBT=0.81 g.
4. BocCys(4-MeBzl); MW 325; 3 mmole=0.97; HOBT=0.81 g.
5. BocAsn; MW 232; 3 mmole=0.70 g; HOBT=1.21 g (9 mmole).
6. BocVal; MW 217; 3 mmole=0.65 g; HOBT=0.81.
7. BocPhe; MW 265; 3 mmole=0.80; HOBT=0.81.
8. (2×) BocD-Tyr(Et); MW 309; 3 mmole=0.92.
9. (3×) Pmp(4-MeBzl); MW 278; 3 mmole=0.83; DMAP 3 mmole.

The resin was sucked dry to yield 3.14 g of peptide resin. All of the peptide resin was treated with 2.0 ml of anisole and 20–30 ml of HF with stirring for 60 minutes at 0°. The HF and anisole were evaporated under reduced pressure at 0°.

The resin was washed with 3×20 ml of ethyl ether (discarded) and the peptide eluted with 5×20 of glacial acetic acid and 2×10 ml of tetrahydrofuran. This was added to 3.5 l of distilled water. The pH was adjusted to 7.2 with ammonium hydroxide. A solution of 0.1M potassium ferricyanide was then added dropwise with stirring until a faint yellow color persisted for 40 minutes (~75 ml).

The pH was adjusted to 4.0 with acetic acid. The solution was filtered, then passed through a flash $C_{18}$ column. The column was washed with water (800 ml) and the peptide was eluted with 50% acetonitrile/water-0.1% trifluoroacetic acid. Those fractions containing peptide were combined, concentrated and lyophilized to yield 310 mg of titled product.

The peptide was further purified over a G-25 partition column (25×100 cm) using butanol/acetic acid/water, 4:1:5, with 200 drops per tube. Peptide-carrying fractions were combined, concentrated, diluted with 0.2N acetic acid and lyophilized to give 120 mg of peptide.

The peptide was then taken through gel filtration on a G-15 column (26×70 cm), eluting with 0.2N acetic acid at 260 drops per tube. Fractions 77–86 were combined and lyophilized to give the 20.1 mg of the titled peptide as the acetate salt.

Amino acid analysis (AAA), Asp (1.00), Gln (0.99), Pro(1.08), Cys (0.14), Val (1.03), Tyr (0.68), Phe (1.07), Arg (0.95); peptide content 78.8%.

FAB mass spectrum: $(M+H)^+$ 1207; $(M-H)^-$ 1205.

EXAMPLE 2

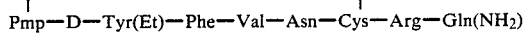

Pmp—D—Tyr(Et)—Phe—Val—Asn—Cys—Arg—Gln($NH_2$)

The titled compound was prepared and purified as detailed above to give 290 mg of white solid; 99% peptide, 97% pure high performances liquid chromatography (HPLC).

EXAMPLE 3

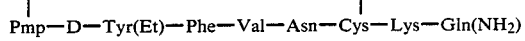

Pmp—D—Tyr(Et)—Phe—Val—Asn—Cys—Lys—Gln($NH_2$)

The titled compound was prepared and purified as detailed above to give 12 mg of white solid; 72% peptide, 95% pure by HPLC.

EXAMPLE 4

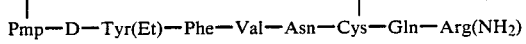

Pmp—D—Tyr(Et)—Phe—Val—Asn—Cys—Gln—Arg($NH_2$)

The resin process of Example 1 was used starting with 1 g of BHA resin using Boc(Arg(Tos)) with HOBT, DCC/DMF and $CH_2Cl_2$ for the first step. 2.4 Grams of dried octapeptide resin was obtained air dried.

The resin was reacted with 2 ml of anisole and 20 ml of hydrogen fluoride as described. The HF was evaporated. The residue was ether washed, extracted twice with 2 ml of trifluoroacetic acid and 10 ml of dimethylformamide, then three more times with 1.5 ml of TFA and 5 ml of DMF. The mixture was put into a degassed mixture of methanol/water, 1:1. The pH was adjusted to 7.2 with triethylamine and the solution cooled. A 1.5 mmole solution of diiodoethane in methanol was added. After standing overnight and stripping, the residue was covered with 500 ml of water. The solid (600 mg) was dried.

200 Mg was passed over a partition column using butanol/acetic acid/water, 4:1:5. The early fractions gave 33 mg which were run in preparative HPLC to give 10 mg of the titled peptide: amino acid analysis (AAA), Asp (1.00), Gln (0.95), Cys (0.49), Val (1.00), Tyr (1.03), Phe (1.08), Arg (0.96). FAB-MS; (M+H)+ 1110, (M−H)− 1108, theoretical molecular weight, 1109.

EXAMPLE 5

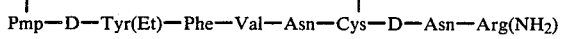

The protected peptide intermediate resin, Pmp(4-MeBzl)-D-Tyr(Et)-Phe-Val-Asn-Cys(4-MeBzl)-D-Asn-Arg(Tos)-BHA is synthesized on 1.0 mmol benzhydrylamine resin as in Example 1. The HF cleavage is carried out and the oxidation with 0.01M potassium ferricyanide is performed as in Example 1 to give the titled peptide.

EXAMPLE 6

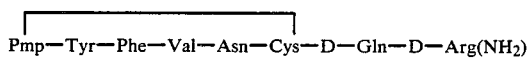

The protected peptide intermediate resin, Pmp-(4-MeBzl)-Tyr(Z)-Phe-Val-Asn-Cys(4-MeBzl)-D-Gln-D-Arg(Tos)-BHA is synthesized on 1.0 mmol of benzhydrylamine resin as in Example 1. The HF cleavage and oxidation with 0.01M potassium ferricyanide are performed similarly to give the titled peptide.

EXAMPLE 7

The protected peptide intermediate resin, Pmp(4-MeBzl)-D-Tyr(Et)-Phe-Val-Asn-Cys(4-MeBzl)-Pro-Gln-Lys(Z)-BHA is synthesized on 1.0 mmol benzhydrylamine resin as in Example 1. The HF cleavage and oxidative cyclization with excess hydrogen peroxide are carried out as described above to give the titled compound.

EXAMPLE 8

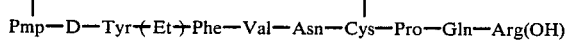

The protected peptide intermediate used, Pmp(4-MeBzl)-D-Tyr(Et)-Phe-Val-Asn-Cys(4-MeBzl)-Pro-Gln-Arg(Tos)-OCH$_2$C$_6$H$_4$-Resin is synthesized on 1.0 mmol of Boc-Arg(Tos)-O-Bzl-Resin (purchased from Peninsula Laboratories). The HF cleavage and oxidation with 0.01M ferricyanide are performed as described above. The dilute solution are purified through a reversed phase silica gel C-18 column, and the peptide is eluted with 50% aqueous CH$_3$CN containing 0.1% TFA to give the titled peptide.

EXAMPLE 9

The protected peptide intermediate resin, Pmp-(4-MeBzl)-Ile-Phe-Val-Asn-Cys(4-MeBzl)-Lys(ClZ)-Gln-BHA is synthesized on 1.0 mmol of benzhydrylamine resin as above. The HF cleavage and oxidation with 0.01M ferricyanide are performed as described to give the titled peptide.

EXAMPLE 10

The titled compound is prepared using the protected linear peptide-resin, splitting with HF-anisole and oxidation with diiodoethane in methanol. Purification is carried out as in Example 4.

EXAMPLE 11

Parenteral Dosage Unit Compositions

A preparation which contains 0.10 mg of the peptide of Example 1 as a sterile dry powder for parenteral injection is prepared as follows: 0.5 mg of peptide is dissolved in 1 ml of an aqueous solution of 20 mg of mannitol. The solution is filtered under sterile conditions into a 2 ml ampoule and lyophilized. The reconstituted solution is administered to a patient in need of vasopressin antagonist treatment as necessary, from 1–5 times daily by injection, or in an equivalent continuous i.v. drip injection.

Nasal Dosage Unit Compositions 2.5 Mg of a finely ground peptide of this invention, such as the product of Example 1, is suspended in a mixture of 75 mg of benzyl alcohol and 1.395 g of a suspending agent such as a commercial mixture of semisynthetic glycerides of higher fatty acids. The suspension is placed in an aerosol 10 ml container which is closed with a metering valve and charged with aerosol propellants. The contents comprise 100 unit doses which are administered intranasally to a subject in need thereof from 1–6 times a day.

What is claimed is:

1. A peptide compound having the formula:

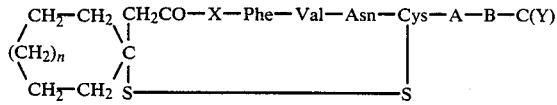

in which:

A is Pro or a single bond;
X is a D or L isomer of Ile, Tyr, Tyr(Alk) or Phe-(Alk);
Y is NH$_2$ or OH;
n is 0 or 1;
B is a D or L isomer of Gln, Asn, Lys or Arg; and
C is a D or L isomer of Gln, Asn, Lys or Arg, one of B and C being either a Gln or Asn and the other being either a Lys or Arg; or a pharmaceutically acceptable salt or ester prodrug thereof.

2. The compound of claim 1 in which B is Gln.

3. The compound of claim 1 in which Y is NH$_2$.

4. The compound of claim 1 in which the compound is [1-($\beta$-mercapto-$\beta$, $\beta$-cyclopentamethylenepropionic acid)-2-(O-ethyl)-D-tyrosine-4-valine-8-glutamine-9-argininamide]vasopressin or a pharmaceutically acceptable, acid addition salt thereof.

5. The compound of claim 1 in which the compound is [1-($\beta$-mercapto-$\beta$,$\beta$-cyclopentamethylenepropionic acid)-2-(O-ethyl)-D-tyrosine-4-valine-7-desproline-8-lysine-9-glutaminamide]vasopressin or a pharmaceutically acceptable, acid addition salt thereof.

6. The compound of claim 1 in which the compound is [1-($\beta$-mercapto-$\beta$,$\beta$-cyclopentamethylenepropionic acid)-2-(O-ethyl)-D-tyrosine-4-valine-7-glutamine-8-arginine-9-desglycine]vasopressin.

7. The compound of claim 1 in which the compound is [1-($\beta$-mercapto-$\beta$,$\beta$-cyclopentamethylenepropionic acid)-2-(O-ethyl)-D-tyrosine-4-valine-7-desproline-8-arginine-9-glutaminamide]vasopressin or a pharmaceutically acceptable, acid addition salt thereof.

8. A pharmaceutical composition having vasopressin antagonist activity comprising a pharmaceutical carrier and, dispersed therein, an effective therefor but nontoxic quantity of a compound of claim 1.

9. A pharmaceutical composition having vasopressin antagonist activity comprising a pharmaceutical carrier and, dispersed therein, an effective therefor but nontoxic quantity of the compound of claim 2.

10. A pharmaceutical composition having vasopressin antagonist activity comprising a pharmaceutical carrier and, dispersed therein, an effective therefor but nontoxic quantity of the compound of claim 4.

11. The method of producing vasopressin antagonist activity in a patient in need thereof which comprises administering parenterally or intranasally to said patient an effective therefor, nontoxic quantity of a compound of claim 1.

12. The method of producing vasopressin antagonist activity in a patient in need thereof which comprises administering parenterally or intranasally to said patient an effective therefor, nontoxic quantity of the compound of claim 2.

* * * * *